(12) United States Patent
Keller

(10) Patent No.: US 6,726,924 B2
(45) Date of Patent: *Apr. 27, 2004

(54) ORAL LIPOSOMAL DELIVERY SYSTEM

(75) Inventor: Brian C. Keller, Antioch, CA (US)

(73) Assignee: Biozone Laboratories, Inc., Pittsburgh, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/148,499

(22) Filed: Sep. 4, 1998

(65) Prior Publication Data

US 2002/0039595 A1 Apr. 4, 2002

Related U.S. Application Data

(60) Provisional application No. 60/057,819, filed on Sep. 4, 1997.

(51) Int. Cl.[7] .......................... A61K 9/127; A61K 9/48; A61K 9/66
(52) U.S. Cl. ....................... 424/450; 424/451; 424/452; 424/453; 424/455; 424/456
(58) Field of Search .................. 424/450, 451–457; 428/402.2

(56) References Cited

U.S. PATENT DOCUMENTS

| | | | | |
|---|---|---|---|---|
| 4,348,384 A | * | 9/1982 | Horikoshi | |
| 4,615,885 A | * | 10/1986 | Nakagami | 424/94.63 |
| 4,619,794 A | * | 10/1986 | Hauser | |
| 4,636,381 A | * | 1/1987 | Takada | 424/450 |
| 5,252,336 A | * | 10/1993 | Iga | 424/450 |
| 5,565,213 A | * | 10/1996 | Nakamori | 424/450 |
| 5,665,379 A | * | 9/1997 | Herslof | 426/450 |
| 5,762,904 A | * | 6/1998 | Okada | |
| 5,876,747 A | * | 3/1999 | Stracher | 424/450 |
| 5,891,465 A | * | 4/1999 | Keller | 424/450 |
| 6,015,576 A | | 1/2000 | See et al. | 424/450 |
| 6,117,449 A | | 9/2000 | See et al. | 424/450 |

FOREIGN PATENT DOCUMENTS

| | | | |
|---|---|---|---|
| EP | 69399 | * | 1/1983 |
| GB | 2002319 | * | 2/1978 |

OTHER PUBLICATIONS

Bangham et al., "Diffusion of Univalent Ions across the Lamellae of Swollen Phospholipids" J. Mol. Biol. (1965) 13, 238–252.

Kirby et al., "Preparation of Liposomes Containing Factor VIII for Oral Treatment of Haemophilia", J. Microencapsulation, 1984, vol. 1, No. 1, pp. 33–45.

Sakuragawa et al., "Oral Administration of Factor VIII Concentrate Preparation In von Willebrand's Disease", Trombosis Research 38, pp. 681–685, 1985.

Woodley, "Liposomes for Oral Administration of Drugs", Critical Reviews in Therapeutic Drug Carrier Systems, vol. 2, Issue 1, 1985.

New et al., "Liposomal Immunisation Against Snake Venoms", Toxicon, vol. 23, No. 2, pp. 215–219, 1985.

Regnault et al., "Pharmacokinetics of Superoxide Dismutase in Rats After Oral Administration", Biopharmaceutics & Drug Disposition, vol. 17, 165–174 (1996).

Ariën et al., "Cholate–Induced Disruption of Calcitonin–Loaded Liposomes: Formation of Trypsin–Resistant Lipid––Calcitonin–Cholate Complexes", Pharmaceutical Research, vol. 12, No. 9, 1995.

Maitani et al., "Oral Administration of Recombinant Human Erythropoietin in Liposomes in Rats: Influence of Lipid Composition and Size of Liposomes on Bioavailablilty", Journal of Pharmaceutical Sciences, vol. 85, No. 4, Apr. 1996.

Lasic, "Liposomes: From Physics to Applications", pp. 88–90, 1993.

* cited by examiner

*Primary Examiner*—Gollamudi S. Kishore
(74) *Attorney, Agent, or Firm*—Morrison & Foerster LLP

(57) ABSTRACT

A liposome-capsule dosage unit system for the delivery of a biologically active material is formed by encapsulating a biologically active materials in liposomes and then placing the liposome encapsulated material into a capsule. The capsule is typically a soft gel capsule or a two piece capsule capable of tolerating a certain amount of water. A less water tolerant capsule can be employed if the liposomes are dehydrated prior to placement within the capsule. Biologically active material include drugs, nutritional supplements, vitamins, minerals, enzymes, hormones, proteins and polypeptides. The system is especially suited for the delivery of materials with poor oral solubility, materials that are not absorbed or are poorly absorbed from the gastrointestinal tract, and materials that have conventionally been given by an invasive route. The system can be administered orally, intra-occularly, intranasally, rectally, or vaginally.

31 Claims, No Drawings

ORAL LIPOSOMAL DELIVERY SYSTEM

This application claims the benefit of 60/057,819 filed on Sep. 4, 1997.

BACKGROUND OF INVENTION

1. Field of Invention

The invention generally relates to the field of liposome based drug delivery systems.

2. Description of Background Art

The therapeutic effect of an administered substance is usually directly related to the quantity and rate ate which the substance reaches the bloodstream. There are many factors that affect the ability of the substance to reach the systemic circulation including; the site of entry into the body, the physical form of the substance, the design of the formulation of the product, various physicochemical properties of the compound and the excipients, and control and maintenance of the location of the substance at the proper absorption site.

Oral delivery of a therapeutic substance is the most common form of delivery today because of convenience and ease of administration, however, it is not the most reliable route of administration and can often be inefficient and erratic. Factors that influence the absorption, and thus the ability of the substance to reach the bloodstream, of an orally administered substance are related to the physicochemical properties or the substance, the physiologic factors in the gastrointestinal tract and the variables in the dosage form. Conventional oral dosage forms consist of solutions, suspensions, powders, two-piece gelatin capsules, soft gelatin capsules, compressed tablets, and coated tablets. It is generally the case that gastrointestinal absorption is most rapid with solutions and progressively slower as you move toward coated tablets in the above continuum. Liquid dosage forms are generally much faster absorbed than solid forms because dissolution is not a rate determining step in the absorption process.

It has long been the idealized object of drug delivery technology to design a dosage form that optimizes effectiveness, maximizes drug reliability and maximizes safety of the delivered compound. Oral dosage forms began to become optimized in the late 1940's and early 1950's when sustained-release technology appeared on the pharmaceutical scene. The principle benefit of this new type of delivery system was to improve drug performance by increasing the duration of drug action and reducing the dosing interval required to achieve a therapeutic effect. Controlled-drug delivery technology, a new concept for improving drug efficacy was developed in the late 1960's. The principle benefit of this technology is to control the rate of dissolution from the solid dosage form to enhance bioavailability, improve safety, and decrease the dosing interval. Within the last twenty years a newer concept in oral drug delivery technology has been developed and is referred to as a therapeutic system. The essential component of the therapeutic system is the incorporation of advanced engineering controls that release drug from the dosage form at appropriate times in response to stimuli, e.g., preprogrammed wax matrix.

Capsules are a convenient and popular solid dosage form used for drugs, vitamins and nutritional supplements worldwide. The drug substance is enclosed within gelatin walls of the capsule, which can be either a two piece hard shell or a soft shell (also known as the soft elastic capsule). The soft elastic capsule (SEC) is a soft, globular, gelatin shell somewhat thicker than that of hard gelatin capsules. The gelatin is plasticized by the addition of glycerin, sorbitol, or a similar polyol. The greatest advantage of soft gel capsule over two piece gelatin capsules is that soft gels can encapsulate liquids, semiliquids, and pastes due to the manufacturing process which hermetically seals the two halves together. There are several manufacturing processes by which soft gel capsules are made, those include the plate process, the rotary die process, the Norton capsule machine and Accogel, or Stern machine. A newer technology allows a two-piece gelatin capsule to tolerate liquids, semiliquids and pastes by sealing the upper and lower pieces together to prevent leakage of encapsulated material.

Liposomes are microscopic, three-dimensional lipid vesicles, made up of a phospholipid bilayer membrane that surrounds and separate an aqueous compartment. The discovery of liposomes has been credited to Alec Bangham, a British biologist and physician, who first described swollen lipid particles in the early 1960's. (Bangham A., et al, J. Mol Biol., 13, 238, 1965). However there is evidence of the observation of multilamellar liposomes dating back to 1911. (Lasic, D., *Liposomes*, 1993). Two decades after Bangham and his colleagues described their discovery the field of liposome science began to take hold, and the pharmaceutical and pharmacological rational that justifies the use of liposomes as drug carriers was being put into practice. Today, the medical applications of liposomes range widely from systemic anticancer therapy to enhancing topical anesthesia and gene delivery.

The use of liposomes orally first begin in the mid 1970's. The attributes of phospholipid based liposomes, e.g., well organized structures able to encapsulate a variety of compounds, with an excellent safety profile, were well known at the time. Medical researchers believed that this would be an ideal application to potentially enhance gastrointestinal absorption, protect the encapsulated ingredient from metabolic degradation and perhaps release the encapsulate slowly, thus providing a form of sustained release. Early studies showed that liposome encapsulated drugs were better absorbed than non-liposome encapsulated or "free" drug. In addition to drug molecules, proteins, peptides and enzymes were delivered orally with liposomes. In an attempt to develop an oral treatment for hemophilia with blood clotting factor VIII, a novel technique was developed which made possible high-yield entrapment of Factor VIII in a liposome. (Gregoridias, G. et al., J. Microencap., 1(1):33–45,1984). Liposomal encapsulated Factor VIII was administered to patients orally and was absorbed from the intestines. (Sakuragawa N., Thrombosis Research 38(6):681–5, 1985). Early enthusiasm with liposome encapsulated insulin showed that small but significant amount of insulin could reach the circulation (Woodly, J F, Critical Rev Ther. Drug Carrier Sys. 2(1):1–18, 1985). Significant antibody response was elicited after oral administration of liposome-entrapped snake venom (enzymes and peptides) compared to no response from free venom. (New, R R, Toxicon. 23(2):215–9, 1985).

More recently, feasibility of oral liposomes for a variety of therapeutic uses has been demonstrated. Increased bioavailability of liposomally encapsulated superoxide dismutase (Regnault C., et al, Biopharm & Drug Disp 17,165–174, 1996) a potent antioxidant used in the treatment of radiation-induced fibrosis, which is poorly absorbed orally, from 14% (free) to 57% with liposomes with ceramides. Hypocalcemia was observed 1 h after the administration of liposomes loaded with 1 mg of calcitonin. (Arien a., et al, Pharm Research 12(9):1289–1292, 1995). This result was surprising because liposomes were presumed to be unstable against the action of bile salts, however they were able to partially protect the peptide from enzymatic degradation. In another study, recombinant human erythropoietin (Epo), used to treat renal anemia, was encapsulated in liposomes. Bioavailability of oral Epo is poor because it is a protein and broken down in the GI tract by proteolytic enzymes. Absorption and a long pharmacological effect and lag were observed, suggesting that liposomes were trapped in a site before entering the bloodstream, and eliciting a sustained release effect. (Maitani Y., J Pharm Sc 85(4):440–445, 1996).

The pharmaceutical related problems associated with administering liposomes orally are: 1) pH of the stomach, 2) bile salts and 3) digestive enzymes, primarily lipases. The unbuffered pH of the stomach can range from 1.5 to 2.5 and causes chemical instability of the liposome membrane surface.

Bile salts act as detergents and cause instability of the liposome bilayer by emulsification. Upon exposure to lipases and other enzymes, the polar head groups or the acyl chains of the phospholipids can be cleaved and thus rupture the liposome vesicle.

DESCRIPTION OF THE INVENTION

Although certain chemical and stearic modifications can be made to liposomes to help stability, the incorporation of a fluid liposome dispersion into a gelatin based capsule can improve stability, provide a convenient dosage form, and assist in sustained release characteristics of the liposome. The present invention broadly relates to a novel delivery system for biologically active material whereby the biologically active material is encapsulated into liposomes or formulated as a preliposome formulation and then put into a capsule. The capsule can be a soft gel capsule capable of tolerating a certain amount of water, a two piece capsule capable of tolerating a certain amount of water or a two piece capsule where the liposomes are preformed then dehydrated. Biologically active material in this invention can be, but is not limited to, drugs, nutritional supplements, vitamins, minerals, enzymes, hormones proteins and polypeptides.

The delivery system of the invention is especially suitable for 1) biologically active materials with poor oral solubility, e.g. morphine, acyclovir, propanolol, fluoxetine, 2) newly discovered drugs, proteins and peptides that are not absorbed or are poorly absorbed from the gastrointestinal tract, and 3) drugs, proteins, hormones and nutrients that can not be absorbed from the GI tract and have to be given by an invasive route such as injection or nasal inhalation, e.g. Vitamin $B_{12}$, calcitonin, insulin, erthropoietin, superoxide dismutase.

The liposome-capsule unit containing biologically encapsulated material can be taken in addition to orally, used for topical unit-of-use application, or other routes of application such as intra-occular, intranasal, rectal, or vaginal.

The liposomes in this invention are comprised of any bilayer forming lipid, which includes phospholipids, sphingolipids, glycosphingolipids, and ceramides. The typical size range of the liposomes is 20 nm–1000 nm. These liposomes can be rehydrated, dehydrated, partially hydrated or fully hydrated. It is also possible to employ a preliposome formulation as the liposome encapsulated biologically active material (liposome-drug complex). This formulation is composed of the biologically active material, phospholipids and cholesterol, and upon contact with water, forms liposomes. The liposomes can be mechanically stabilized using certain phospholipids, e.g. phospholipon 90H, and cholesterol at an optimum molar ratio of 2:1. The optimum ratio is expected to vary with the specific phospholipid selected. This stability can protect the liposome from GI degradation.

Gelatin capsules have a lower tolerance to water on their interior and exterior. The usual water tolerance for a soft gel capsule is 10% on the interior. The concentration of water in a liposome formulation can range from 60–90% water. An essential component of the present invention is the formulation of a liposome with a relatively small amount of water, in the range of 5–10%. By making the liposome in a low aqueous system, the liposome is able to encapsulate the biologically active material and the exposure of water to the inside lining of the capsule is limited. The concentration of water should not exceed that of the tolerance of the capsule for which it is intended. The preferred capsule for this invention is one that can tolerate water in the 15–20% range.

The capsulation of liposomes into a gelatin shell improves the stability of the liposome because it is protected from exposure to the air and thus oxidation. This increases the shelf life of the product. Capsulation will also initially protect the liposome-drug complex from the low pH of the stomach, emulsification from bile salts and degradation of the liposomes and the drug substance by digestive enzymes. This protection can be further enhanced when the outer shell of the capsule is coated with a polymer like hydroxyethylmethyl cellulose propylethyl acetate, or hydroxypropylmethylcellulose propylethyl thallate.

In the past, all administration of oral liposomes have been as a liquid, given by intubation directly into the small intestine, to the back of the throat by a gavage syringe or by dropper directly into the mouth. These are very impractical ways of administering therapeutic agents because they can be messy, provide an inaccurate dose, and are difficult for patients to handle. In addition many biologically active ingredients have a bitter, astringent and unpleasant taste that is unpalatable and difficult to mask. Liposomes in a capsule dosage form provide a convenient, easy to manage unit-of-use which can be more easily handled by the patient than the usual liquid form of a liposome preparation. An easy to take dosage form, such as a capsule, leads to increased compliance by the patient. Noncompliance is disturbingly common. Over one-half of the 1.6 billion prescriptions written annually in the U.S. are taken incorrectly, and 30–50% of the prescribed medications fail to produce their intended results. The economic consequences of medication noncompliance is in excess of $100 billion annually. A significant barrier to compliance is regimen complexity. Reduction of regimen complexity includes use of convenient dosing formulations. It is estimated that 50% of the American population don't like taking oral liquids. By administering a liposome in a capsule, certain compliance issues are overcome. There has been very little discussion or development of an oral dosage form for liposomes up until now and there are no commercial oral liposome dosage forms available.

The gel caps best used for this invention range in size and shape. The various shapes include, but are not limited to, oval, oblong, cylindrical, round and torpedo shaped. Size of soft elastic capsules is measured by the amount of liquid that can fit into the capsule. The size range of soft gel capsules in this invention is 0.045 cc (0.75 minims) to 5 cc (81.2 minims). The typical size range of two piece capsules is from 600 mg to 30 mg; these capsules are numbered from 000, the largest, to 5, the smallest.

EXAMPLES

Example 1

| Vitamin B$_{12}$ LipoCap Formulation | |
|---|---|
| Ingredient | Concentration (%) |
| Purified water, USP | 10 |
| Cyanocobalamin, USP | 0.345 |
| Phospholipon 90H (DPPC) | 3 |
| Cholesterol, NP | 2 |
| Vitamin E, USP | 1 |
| Benzyl Alcohol, NF | 1 |
| Propylene glycol, USP | 82.655 |

Components are commingled and liposomes are made using the injection method (Lasic, D., *Liposomes*, Elsevier, 88–90, 1993). When liposome mixture cooled down 0.7 ml was drawn into a 1 ml insulin syringe and injected into the open-end of a soft gelatin capsule then sealed with tweezers. The resulting capsule contains 2500 mcg of Vitamin B$_{12}$. Large scale manufacturing methods for filling gel caps, such as the rotary die process, are the preferred method for commercial applications.

Example 2

| Co-Enzyme Q$_{10}$ LipoCap Formulation | |
|---|---|
| Ingredient | Concentration |
| Purified water, USP | 5 |
| Phospholipon 90H (DPPC) | 5 |
| Cholesterol, NF | 3 |
| Vitamin E, USP | 1 |
| CoQ$_{10}$ | 1.29 |
| Potassium Sorbate, NF | 1 |
| Propylene glycol, USP | 84.46 |

Components are commingled and liposomes are made using the injection method (Lasic, D., *Liposomes*, Elsevier, 88–90, 1993). When liposome mixture cooled down 0.7 ml was drawn into a 1 ml insulin syringe and injected into the open-end of a soft gelatin capsule then sealed with tweezers. The resulting capsule contains 10 mg CoQ10. Filling of gel caps on a large scale is best with the rotary die method or others such as the Norton capsule machine.

Example 3

| Vitamin E LipoCap Formulation | |
|---|---|
| Ingredient | Concentration (%) |
| Sorbitan Oleate | 2.0 |
| Vitamin E, USP | 89.8 |
| Purified Water | 4.0 |
| Potassium Sorbate | 0.2 |
| Polysorbate 20 | 2.0 |
| Phospholipon 90 (DPPC) | 2.0 |

Components are commingled and liposomes are made using the injection method (Lasic, D., *Liposomes*, Elsevier, 88–90, 1993). When liposome mixture cooled down 0.7 ml was drawn into a 1 ml insulin syringe and injected into the open-end of a soft gelatin capsule then sealed with tweezers. The resulting one gram capsule contains 898 IU of Vitamin E. Large scale manufacturing methods for filling gel caps, such as the rotary die process, are the preferred method for commercial applications.

Example 4

| L-Carnitine LipoCap Formulation | |
|---|---|
| Ingredient | Concentration |
| Propylene Glycol | 3.0 |
| Lycosin-75$^R$ (Roquette) | 73.5 |
| L-Carnitine | 20.0 |
| Phospholipon 80H (DPPC) | 3.5 |

Components are commingled and liposomes are made using the injection method (Lasic, D., *Liposomes*, Elsevier, 88–90, 1993). When liposome mixture cooled down 0.7 ml was drawn into a 1 ml insulin syringe and injected into the open-end of a soft gelatin capsule then sealed with tweezers. The resulting one gram capsule contains 735 mg of L-Carnitine. Filling of gel caps on a large scale is best with the rotary die method or others such as the Norton capsule machine.

What is claimed is:

1. A method for preparing a liposome formulation in a gelatin capsule, comprising:
   formulating a liposome dispersion, wherein said liposome dispersion is formulated by mixing a lipid component, an active ingredient component, a water component, and an oil component such that said dispersion comprises liposomes in a fluid medium, wherein said fluid medium comprises said water and said oil components; and
   directly inserting the liposome dispersion into the capsule.

2. The method of claim 1, wherein the lipid is selected from the group consisting of phospholipids, sphingolipids, glycosphingolipids, and ceramides.

3. The method of claim 1, wherein the capsule is a soft gel capsule.

4. The method of claim 1, wherein the capsule is composed of two pieces.

5. The method of claim 1, wherein the biologically active material is selected from the group consisting of drugs, nutritional supplements, vitamins, minerals, enzymes, hormones, proteins, and peptides.

6. A liposome formulation in a capsule prepared by the process of claim 1.

7. The method of claim 1, wherein the oil component comprises Vitamin E.

8. The method of claim 1, wherein said fluid medium comprises a low aqueous system.

9. The method of claim 1, wherein said water component comprises no greater than about 10% of the total fluid medium.

10. The method of claim 1, wherein said water component comprises about 4% to 10% of the total fluid medium.

11. The method of claim 1, wherein said water concentration within the total fluid medium does not exceed the water tolerance of the gelatin capsule.

12. The capsule of claim 6, wherein the lipid is selected from the group consisting of phospholipids, sphingolipids, glycosphingolipids, and ceramides.

13. The capsule of claim 6, wherein the active material selected from the group consisting of drugs, nutritional supplements, vitamins, minerals, enzymes, hormones, proteins, and peptides.

14. The capsule of claim 6, wherein the capsule is a soft gel capsule.

15. The capsule of claim 6, wherein the capsule is composed of two pieces.

16. A capsule for delivering an active ingredient to a subject comprising a liposome dispersion, wherein said liposome dispersion comprises a lipid component, an active ingredient component, a water component, and an oil component such that said dispersion comprises liposomes in a fluid medium, wherein said fluid medium comprises said water and said oil components.

17. The capsule of claim 16, wherein the oil component comprises Vitamin E.

18. The capsule of claim 16, wherein said fluid medium comprises a low aqueous system.

19. The capsule of claim 16, wherein said water component comprises a concentration no greater than about 10% of the total fluid medium.

20. The capsule of claim 16, wherein said water component comprises about 4% to 10% of the total fluid medium.

21. The capsule of claim 16, wherein said water concentration within the total fluid medium does not exceed the water tolerance of the gelatin capsule.

22. The method of claim 16, wherein the lipid is selected from the group consisting of phospholipids, sphingolipids, glycosphingolipids, and ceramides.

23. The method of claim 16, wherein the active material selected from the group consisting of drugs, nutritional supplements, vitamins, minerals, enzymes, hormones, proteins, and peptides.

24. The method of claim 16, wherein the capsule is a soft gel capsule.

25. The method of claim 16, wherein the capsule is composed of two pieces.

26. A method for administering a biologically active material to a subject, which method comprises introducing a capsule to the subject by oral administration, wherein:

the capsule comprises a liposome dispersion; and the liposome dispersion comprises a lipid component, an active ingredient component, a water component, and an oil component such that said dispersion comprises liposomes in a fluid medium, wherein said fluid medium comprises said water and said oil components.

27. The method of claim 26, wherein the oil component comprises Vitamin E.

28. The method of claim 26, wherein said fluid medium comprises a low aqueous system.

29. The method of claim 26, wherein said water component comprises no greater than about 10% of the total fluid medium.

30. The method of claim 26, wherein said water component comprises about 4% to 10% of the total fluid medium.

31. The method of claim 26, wherein said water concentration within the total fluid medium does not exceed the water tolerance of the gelatin capsule.

* * * * *